(12) United States Patent
Kleyman

(10) Patent No.: US 12,721,679 B1
(45) Date of Patent: Sep. 1, 2026

(54) APPARATUS FOR TARGETED TISSUE AREA ABLATION

(71) Applicant: Gennady I Kleyman, Brooklyn, NY (US)

(72) Inventor: Gennady I Kleyman, Brooklyn, NY (US)

( * ) Notice: Subject to any disclaimer, the term of this patent is extended or adjusted under 35 U.S.C. 154(b) by 0 days.

(21) Appl. No.: 19/438,141

(22) Filed: Dec. 31, 2025

(51) Int. Cl.
*A61B 18/18* (2006.01)
*A61B 18/00* (2006.01)

(52) U.S. Cl.
CPC .................... *A61B 18/1815* (2013.01); *A61B 2018/00077* (2013.01); *A61B 2018/00083* (2013.01); *A61B 2018/00095* (2013.01); *A61B 2018/0013* (2013.01); *A61B 2018/00178* (2013.01); *A61B 2018/00184* (2013.01); *A61B 2018/00494* (2013.01); *A61B 2018/00529* (2013.01); *A61B 2018/00541* (2013.01); *A61B 2018/00577* (2013.01)

(58) Field of Classification Search
CPC ...... A61B 18/1815; A61B 2018/00077; A61B 2018/00083; A61B 2018/00095; A61B 2018/0013; A61B 2018/00178; A61B 2018/00184; A61B 2018/00494; A61B 2018/00529; A61B 2018/00541; A61B 2018/00577
See application file for complete search history.

(56) References Cited

U.S. PATENT DOCUMENTS

| | | | | |
|---|---|---|---|---|
| 6,773,409 | B2 * | 8/2004 | Truckai | A61B 18/1815 606/49 |
| 8,343,144 | B2 * | 1/2013 | Kleyman | A61B 18/1815 606/33 |
| 10,004,552 | B1 * | 6/2018 | Kleyman | A61B 18/1815 |
| 10,531,918 | B2 * | 1/2020 | Hancock | A61B 18/1815 |
| 2010/0249769 | A1 * | 9/2010 | Nau, Jr. | A61B 18/1815 606/33 |
| 2024/0099764 | A1 * | 3/2024 | Kleyman | A61B 18/1445 |
| 2026/0069347 | A1 * | 3/2026 | Kleyman | A61B 18/1445 |

* cited by examiner

*Primary Examiner* — Michael F Peffley

(57) ABSTRACT

A surgical ablation apparatus and method are disclosed for delivering controlled and uniform thermal energy to a target tissue area. The apparatus includes a heating element having a heating body formed from a microwave-absorbing material and a microwave antenna disposed entirely within the heating body. The microwave antenna is configured to distribute microwave energy substantially uniformly throughout the volume of the microwave-absorbing material, thereby converting microwave energy into heat for tissue ablation. The heating body may have planar, rectangular, curved, dome-shaped, or other geometries adapted to conform to planar or non-planar anatomical tissue surfaces. The microwave antenna may include spiral, serpentine, zig-zag, loop, linear, microstrip, or other antenna configurations shaped to follow the geometry of the heating body. The heating element may be incorporated into forceps-based instruments, planar applicator devices, or other surgical tools to provide uniform thermal delivery and predictable tissue ablation zones.

20 Claims, 6 Drawing Sheets

40
32
36
HEATING AREA
50

40
38
32
36
34
50

40
32
36

50
36
34

42
36
34

APPARATUS FOR TARGETED TISSUE AREA ABLATION

FIELD OF THE INVENTION

The invention relates to electrosurgical apparatus, including metal-jaw structures and planar surgical instruments, for use in open and laparoscopic procedures to perform targeted tissue ablation and related methods.

BACKGROUND TO THE INVENTION

Conventional open and laparoscopic ablation procedures rely on instruments that deliver energy through point-based probes, needles, wires, or narrow jaw structures. These devices generate small, localized ablation zones and require repeated repositioning to treat a broader tissue region. As a result, achieving uniform and controlled area ablation over a defined planar surface—or over a more complex, contoured tissue surface—is difficult, often leading to inconsistent ablation depth, prolonged procedure times, and increased risk of collateral thermal spread.

Existing electrosurgical, microwave, and radiofrequency systems are generally configured with cylindrical or small-profile applicators that are not optimized for broad tissue contact. Such geometries inherently limit the ability to create a large, predictable ablation footprint. Surgeons performing organ resections or tumor debunking must therefore rely on multiple overlapping ablations, which may compromise precision and produce irregular zones of necrosis.

U.S. Pat. No. 8,343,144 provides a jaw structure configured with an antenna or applicator, for the delivery of electromagnetic energy in microwave range to a jaw structure, in which the portion of the jaw structure that is made out of the material impregnated with particles or fillers that absorb electromagnetic energy. During the process of absorption of the microwave energy, microwave absorbing material is transferred microwave energy into the heat. The generated heat is applied to the treated tissue by means of capturing the tissue in the jaw structure and applying pressure on the tissue, thus causing, depending on the used medical procedure, the sealing of the tissue or vessels, or welding and coagulation of the tissue.

Despite the operational benefits associated with the device disclosed in U.S. Pat. No. 8,343,144, its structure confines ablation to a narrow, line-shaped region. The device lacks the capability to produce a uniform, controlled ablation over an extended or planar tissue area.

U.S. Pat. No. 9,333,034 relates to an electrosurgical apparatus that delivers both radiofrequency (RF) and microwave energy for treating biological tissue. Specifically, the device utilizes RF energy for tissue cutting and microwave energy for hemostasis and vessel sealing.

A primary disadvantage of the technology disclosed in this patent is that the apparatus is not designed to ablate a broad tissue area. Its configuration and energy-delivery mechanism limit treatment to localized zones, preventing effective ablation of a large, uniform target region.

Accordingly, there remains a need for an ablation instrument capable of delivering controlled, uniform, and reproducible energy across a defined target tissue area. Such an instrument should enable rapid and consistent area ablation in a single activation, without requiring repeated repositioning of the device.

SUMMARY OF THE INVENTION

The present invention addresses at least the above-described problems and/or disadvantages and provides at least the advantages described below.

According to one aspect of the present invention, a metal forceps device is provided having opposing jaws configured to compress, heat, and ablate a targeted tissue area. The jaw structure incorporates an antenna for delivering electromagnetic energy in the microwave frequency range, the antenna being fully enclosed within one or more microwave-absorbing materials to ensure controlled and uniform energy distribution across the contacted tissue surface. The microwave-absorbing material typically comprises a substrate impregnated with particles or fillers that absorb electromagnetic energy. During absorption of the microwave energy emitted by the antenna, the absorbing material converts the electromagnetic energy into heat, which is conducted to the adjacent tissue. The shape and size of the microwave-absorbing material portion within the forceps jaws may vary—such as cylindrical, rectangular, oval, or other geometries—depending on the size and shape of the targeted treatment area, and different forceps configurations may therefore incorporate different shapes or sizes of the microwave-absorbing material portion. To achieve controlled, uniform, and reproducible ablation across a defined tissue region, the microwave antenna is constructed with a configuration adapted to direct and distribute microwave energy evenly into the entire volume of the microwave-absorbing material, thereby ensuring consistent thermal delivery at the tissue-contacting surface. To achieve controlled, uniform, and reproducible ablation across a defined tissue region, the microwave antenna is configured with a non-linear geometry designed to direct and distribute microwave energy evenly throughout the full volume of the microwave-absorbing material. This configuration ensures consistent thermal delivery at the tissue-contacting surface and promotes uniform heating of the targeted tissue area.

In various embodiments, the microwave antenna may be formed as a coaxial spiral antenna, a coaxial antenna incorporating a rectangular, oval, zig-zag, serpentine, or otherwise contoured geometry, or any other non-linear or multi-directional layout suitable for distributing microwave energy across the microwave-absorbing material. The antenna may additionally be implemented as a linear, quasi-linear, folded, loop-type, slot-type, or other microwave antenna structure capable of directing electromagnetic energy into substantially all regions of the microwave-absorbing material.

These antenna geometries and configurations allow energy to be delivered in a manner that minimizes hot spots, reduces localized overheating, and ensures that the microwave-absorbing material is excited uniformly, thereby supporting predictable and reproducible ablation performance over a planar or shaped jaw surface.

According to another embodiment of the present invention, a planar applicator device is provided having a generally planar body configured to contact a targeted tissue surface and to heat and ablate a defined tissue area. The planar applicator incorporates an antenna adapted for delivering electromagnetic energy in the microwave frequency range, the antenna being fully enclosed within one or more microwave-absorbing material portions to promote controlled, uniform, and reproducible energy distribution across the tissue-contacting surface.

The planar body may be fabricated in a variety of geometries depending on the intended clinical application, including but not limited to a flat planar surface, a slightly curved or contoured surface, a dome-shaped profile, a concave profile, or other three-dimensional shapes configured to follow the anatomical profile of the targeted tissue region.

The internal antenna structure may be selected from a wide range of microwave antenna configurations capable of distributing electromagnetic energy uniformly into the surrounding microwave-absorbing material. Suitable antenna geometries include, but are not limited to, coaxial spiral antennas, meander-line and serpentine antennas, loop and folded-loop antennas, zig-zag patterns, and rectangular, oval, or other shaped coaxial segments. The antenna may also be implemented as a flat microwave radiator, such as a microstrip patch antenna. In further embodiments, the heating assembly may incorporate alternative flat or curved antenna configurations-including planar loop structures, curved or contoured microstrip patterns, or other two-dimensional or three-dimensional conductive geometries-adapted to conform to the applicator's shape and provide uniform energy distribution across the desired ablation footprint.

The microwave-absorbing material may comprise a polymeric, ceramic, elastomeric, composite, or other dielectric substrate impregnated with microwave-absorbing particles or fillers. The thickness, density, and overall geometry of the microwave-absorbing material portion may be varied to achieve a controlled thermal gradient, improve uniformity of energy deposition, or adapt the applicator to different tissue thicknesses. The external surface of the microwave-absorbing material may be smooth, planar, textured, or contoured to enhance tissue contact and heat transfer.

In certain embodiments, the planar applicator may further incorporate optional integrated features such as temperature sensors, thermal feedback elements, embedded thermocouples, microwave power sensors, or thermal insulation layers to regulate energy delivery and prevent excessive heating of adjacent non-target tissue. Cooling channels, thermal spread-reducing structures, or reflective shielding layers may also be integrated to optimize thermal performance.

The structure, composition, and configuration of the microwave-absorbing material and the internal antenna may be similar to, or derived from, the microwave-absorbing structures described herein for the forceps-type tissue area ablation device, thereby enabling a consistent and predictable ablation profile across a large and well-defined tissue area.

Microwave energy is delivered to the antenna through a coaxial transmission line operatively coupled to an external microwave generator. The transmission line may include a variety of coaxial cable types, such as standard coaxial cable, low-loss coaxial cable, semi-rigid or conformable coaxial cable, or other microwave-grade coaxial conductors configured to provide stable power delivery, controlled impedance, and minimal signal attenuation. Selection of the coaxial cable type may be based on the required flexibility, thermal performance, insertion loss, and overall instrument geometry.

BRIEF DESCRIPTION OF THE DRAWING

The above and other aspects, features and advantages of the present invention will become more apparent from the following detailed description when taken in conjunction with the accompanying drawing in which.

DETAILED DESCRIPTION

Figure 1:
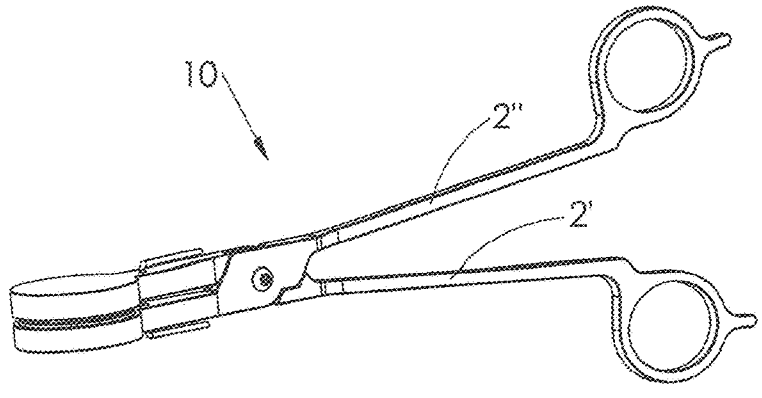
FIG. 1 illustrates a perspective view of one embodiment of the forceps assembly (10), shown with the forceps in a closed position.

In the associated figures together with the description herein, these and other features and advantages of exemplary embodiments of the present invention are set forth. Various embodiments of the present invention are described in detail with reference to the accompanying drawings. Wherever possible, the same or similar reference numerals are used in the drawings and the description to refer to the same or like parts or steps. In the following description, specific details are provided to provide an overall understanding of embodiments of the present invention and those skilled in the art will recognize that various changes and modifications of the embodiments described herein can be made without departing from the scope and spirit of the invention. Descriptions of well-known functions and constructions are omitted for the sake of clarity and conciseness.

In this specification "microwave" may be used broadly to indicate a frequency range of 300 MHz to 100 GHz, but preferably the range 1 GHz to 60 GHz. Specific frequencies that have been considered applicable (but not limited to) here are: 915 MHz, 2.45 GHz, 3.3 GHZ, 5.8 GHz, 10 GHz, 14.5 GHz and 24 GHz.

The heating elements described herein are preferably constructed from microwave-absorbing materials that can be formed by extrusion, injection molding, machining, casting, or other suitable manufacturing processes. The microwave-absorbing material may comprise silicone or other elastomeric or thermoplastic matrices impregnated with conductive or dielectric fillers configured to absorb microwave energy and convert it into thermal energy.

In one embodiment, the microwave-absorbing material is silicone impregnated with silver (Ag) particles and glass fillers. Such materials are resistant to thermal degradation and remain stable at temperatures up to approximately 500° F. The glass fillers may include spherical glass beads, milled fibers, or other particulate forms. Additional optional fillers include nickel (Ni), copper (Cu), aluminum (Al), or combinations thereof, such as Ag/Cu, Ag/Al, Ag/Ni, Ag/glass, or other hybrid filler systems that optimize microwave absorption, thermal generation, and mechanical stability.

Silicone is a preferred matrix material due to its biocompatibility, thermal stability, and processing versatility. However, other elastomeric or thermoplastic materials may also be used. These include fluorosilicone, fluorocarbon elastomers, monoplastic rubbers, and ethylene-propylene-diene monomer (EPDM). Thermoplastic materials may also be employed, such as rigid urethane impregnated with polyamide, thermoplastic urethane impregnated with carbonyl iron powder, iron silicide, ferrite fillers, or other microwave-responsive particulate additives. In still other embodiments, ceramic materials containing ferrite, powdered metal, or mixed dielectric fillers may be utilized to achieve advantageous microwave-absorbing properties.

During operation, microwave energy emitted by an internal or embedded microwave antenna is absorbed by the microwave-absorbing material and converted into heat. The resulting thermal energy is conveyed to the targeted biological tissue when the applicator or jaw structure is applied to the tissue. Depending on the surgical procedure, the tissue may be compressed between opposing jaws or engaged directly by a planar applicator surface, thereby enabling predictable heating and ablation across a defined tissue area.

According to another embodiment of the present invention, a planar applicator device is provided. The planar applicator device includes a generally planar body configured with heating element to contact a targeted tissue surface and deliver controlled heating and ablation over a defined tissue footprint. The internal heating element antenna structure may be selected from coaxial, spiral, loop, serpentine, microstrip patch, or other microwave antenna geometries capable of distributing electromagnetic energy uniformly into the surrounding microwave-absorbing material.

Microwave energy for use with the described devices may be supplied by a variety of commercially available medical microwave generators. Examples include, but are not limited to:

- the Solero® microwave generator by AngioDynamics operating at 2.45 GHz;
- the Emprint™ HP ablation generator by Medtronic; and
- the Certus 140™ generator by Neuwave.

These generators or other compatible microwave energy sources may be coupled to the antenna through appropriate coaxial cables or waveguide connections.

Microwave energy is delivered from the microwave generator to the internal microwave antennas through one or more coaxial cables, preferably low-loss or ultra-low-loss coaxial cables to minimize power attenuation and maintain consistent energy delivery. Suitable low-loss coaxial cables may be fabricated by commercially available manufacturers, including but not limited to companies such as Times Microwave Systems, Pasternack, MECA Electronics, and other medical-grade or high-frequency cable suppliers capable of producing 2.45 GHZ and higher-frequency microwave transmission lines.

The heating elements may be retained within the undercut structures using high-temperature adhesives, such as high-heat epoxies including, for example, 3M™ Scotch-Weld™ DP760, 3M™ Scotch-Weld™ EC-2216, Loctite® EA 9340, or other epoxies capable of withstanding temperatures exceeding 250-300° C. Alternatively, the heating elements may be secured by mechanical clamping, press-fit or interference-fit retention, or other suitable mechanical fastening arrangements designed to maintain stable positioning during thermal cycling and surgical use.

In certain embodiments, the forceps or planar applicator device may further incorporate optional integrated features, such as temperature sensors, thermal feedback elements, or embedded thermocouples configured to monitor and control the temperature of the heating elements (not shown). Additional sensing technologies may also be used, including resistance temperature detectors (RTDs), infrared (IR) sensors, or fiber-optic temperature sensors capable of providing real-time thermal data during tissue ablation.

In some embodiments, the sensor outputs may be integrated into a closed-loop feedback system that adjusts microwave power delivery to maintain a desired temperature profile across the heating elements and the contacted tissue region. Such control systems can provide enhanced safety by preventing overheating, initiating automatic power reduction, or temporarily interrupting microwave energy delivery when predetermined thermal thresholds or safety limits are exceeded.

In some embodiments the heating element may be provided with a thin, biocompatible, non-stick coating layer, such as polytetrafluoroethylene (PTFE, e.g., Teflon®), or other fluoropolymer coatings. Such coatings can reduce the potential for biological material to adhere to the applicator during use and assist in preventing bacterial accumulation. The coating layer is typically applied as a thin film, with a representative thickness ranging from approximately 0.0003 inches to 0.0006 inches per surface, although other thicknesses may be used depending on the specific material and desired functional properties.

Figure 2:
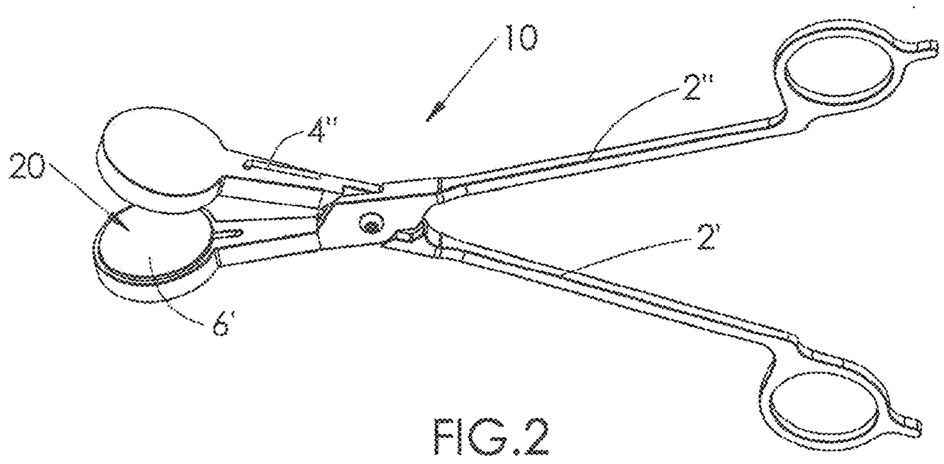
FIG. 2 illustrates a perspective view of one embodiment of the forceps assembly (10), shown with the forceps in an open position.

In some embodiments the heating elements may be fabricated in alternative shapes—including, but not limited to, rectangular, square, elliptical, or other suitable cross-sections—to better conform to the profile of the targeted tissue area for ablation, without departing from the scope of the present disclosure In FIG. 1 and FIG. 2, perspective views of the forceps assembly (10) are shown in the open and closed states, each incorporating cylindrical heating elements (20). However, it will be understood that the structural concept of the forceps is not limited to this geometry. The heating elements may be fabricated in alternative shapes—including, but not limited to, rectangular, square, elliptical, or other suitable cross-sections—to better conform to the profile of the targeted tissue area for ablation, without departing from the scope of the present disclosure.

Figure 3:
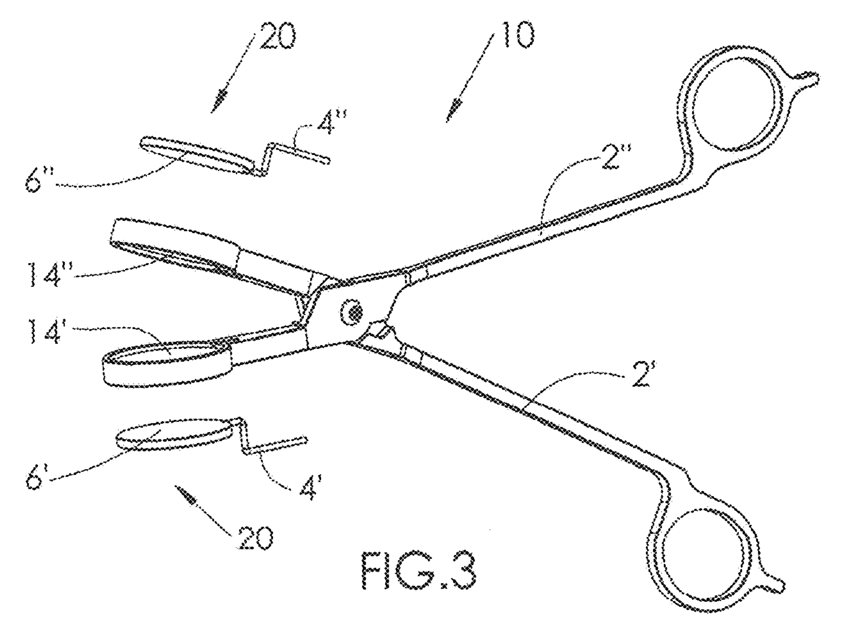
FIG. 3 is an exploded view of one embodiment of the forceps assembly (10).

FIG. 3 illustrates an exploded view of the forceps assembly (10). The assembly comprises opposing jaws (2') and (2"), preferably manufactured from surgical-grade stainless steel. Each jaw includes an undercut structure (14') and (14") configured to receive and secure the corresponding heating elements (20). On these figures, portions of coaxial cables (4') and (4") are shown, which deliver microwave energy to the heating elements (6') and (6").

Figures 4, 5, 6, 7, 8, 9:
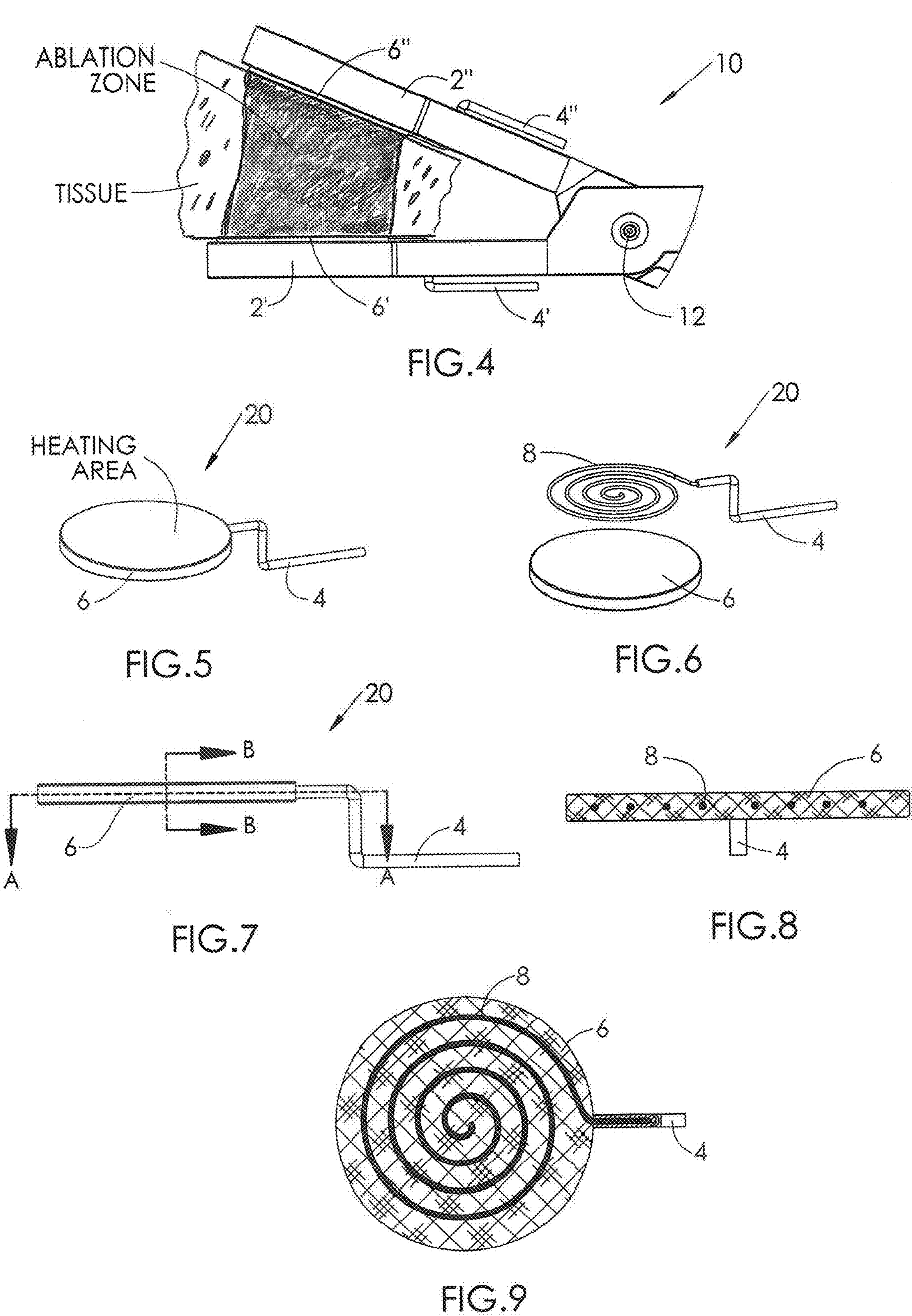
FIG. 4 is a view of the forceps assembly (10), shown with the jaws compressing a target tissue region and depicting an illustrative example of the resulting tissue ablation zone.
FIG. 5 illustrates a perspective view of the cylindrical heating elements (20) from forceps assembly (10) according to one embodiment of the present invention.
FIG. 6 is an exploded view of cylindrical heating elements (20).
FIG. 7 is a front view of cylindrical heating elements (20).
FIG. 8 is a cross-sectional view taken along line B-B from FIG. 7.
FIG. 9 is a cross-sectional view taken along line A-A from FIG. 7.

FIG. 4 is a view of the forceps assembly (10), shown with the jaws (2') and (2") compressing a target tissue region and depicting an illustrative example of the resulting tissue ablation zone. The ablation zone corresponds to the region of thermal energy delivered by the heating elements (6') and (6").

FIG. 5 through FIG. 9 illustrates various views and cross-sections of the heating element structure (20). Each cylindrical heating element (20) comprises a heating body (6) formed from a microwave-absorbing material, within which a spiral microwave antenna (8) is incorporated. A coaxial cable (4) is connected to the antenna (8) to deliver microwave energy into the heating body (6).

The microwave antenna (8) is configured to distribute microwave energy uniformly throughout the volume of the heating body (6), thereby ensuring reliable and consistent ablation across the targeted tissue area. The diameter of the heating body (6) may vary depending on the specific application and target tissue geometry, and may range, without limitation, from approximately 5 millimeters to 40 millimeters.

The microwave antenna (8) may be embedded within the microwave-absorbing material of the heating body (6) using overmolding techniques or other suitable fabrication methods, such as insert molding, potting, encapsulation, or press-fitting the antenna assembly into a pre-formed cavity. These methods enable precise alignment and stable integration of the antenna within the heating body during repeated thermal cycling and surgical use.

The thickness of the microwave-absorbing material used to form the heating body (6) may vary depending on the type of tissue targeted for ablation, the desired ablation depth, and the composition of the microwave-absorbing material. In particular, the thickness may be selected based on the type, concentration, and density of the filler particles impregnated within the elastomeric or thermoplastic matrix. In various embodiments, the thickness of the heating body may range from approximately 2 millimeters to 10 millimeters, although greater or lesser thicknesses may be employed as needed to achieve the desired thermal performance and energy absorption characteristics.

FIGS. 6, 8, and 9 illustrate exemplary embodiments in which the microwave antenna 8 is disposed within the heating body (6) of the heating element (20). The antenna geometry and placement are selected to distribute microwave energy substantially uniformly throughout the heating body (6), ensuring consistent volumetric heating and reliable ablation of the entire tissue area in contact with the heating element.

Figures 10, 11, 12, 13, 14:
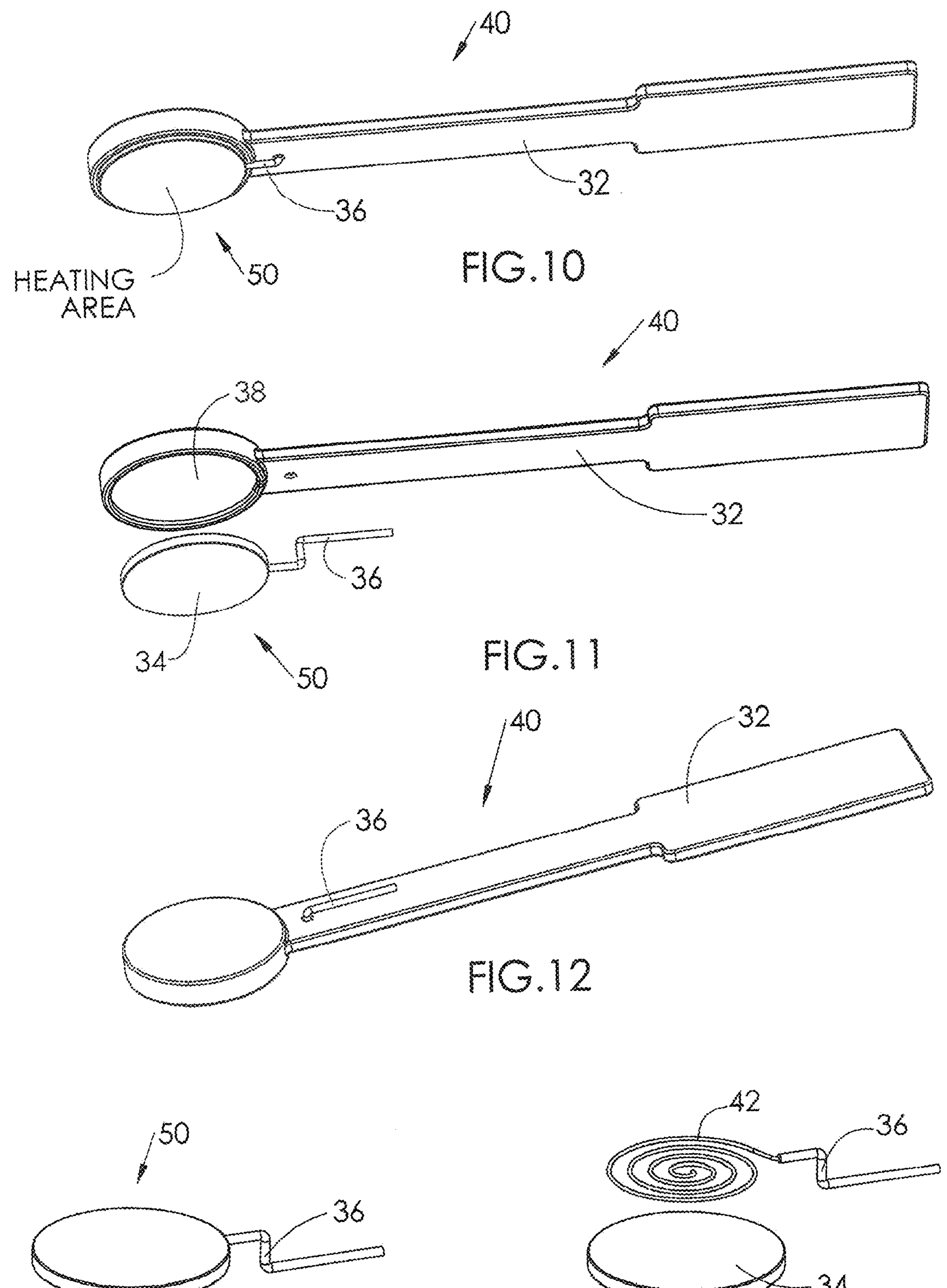
FIG. 10 illustrates a perspective view of one embodiment of the planar applicator device assembly (40).
FIG. 11 illustrates an exploded view of embodiment of the planar applicator device assembly (40).
FIG. 12 illustrates a perspective view from a second perspective, of the planar applicator device assembly (40).
FIG. 13 illustrates a perspective view of the cylindrical heating elements (50) planar applicator device assembly (40).
FIG. 14 is an exploded view of cylindrical heating elements (50).

FIGS. 10, 11, and 12 illustrate alternative embodiments of a planar applicator device assembly (40), configured in a manner analogous to the forceps-based heating assemblies described herein. The planar applicator includes an applicator body (32), preferably formed from surgical-grade stainless steel or other biocompatible materials, and a heating element (50) secured to a distal portion of the applicator body (32).

A coaxial cable (36) is operatively coupled to a source of microwave energy and, as shown in FIGS. 13 and 14, delivers microwave energy to a microwave antenna (42) disposed entirely within a heating body (43). The heating body (43) is formed from a microwave-absorbing material and is configured to convert the delivered microwave energy into heat for controlled, uniform, and reproducible tissue ablation across a defined planar tissue contact area.

The internal microwave antenna (42) may comprise a spiral, serpentine, planar, or other non-linear antenna geometry selected to distribute microwave energy substantially uniformly throughout the volume of the heating body (43), thereby ensuring consistent thermal delivery and reliable ablation of the tissue area contacted by the heating element (50).

Figures 15, 16, 17, 18, 19:
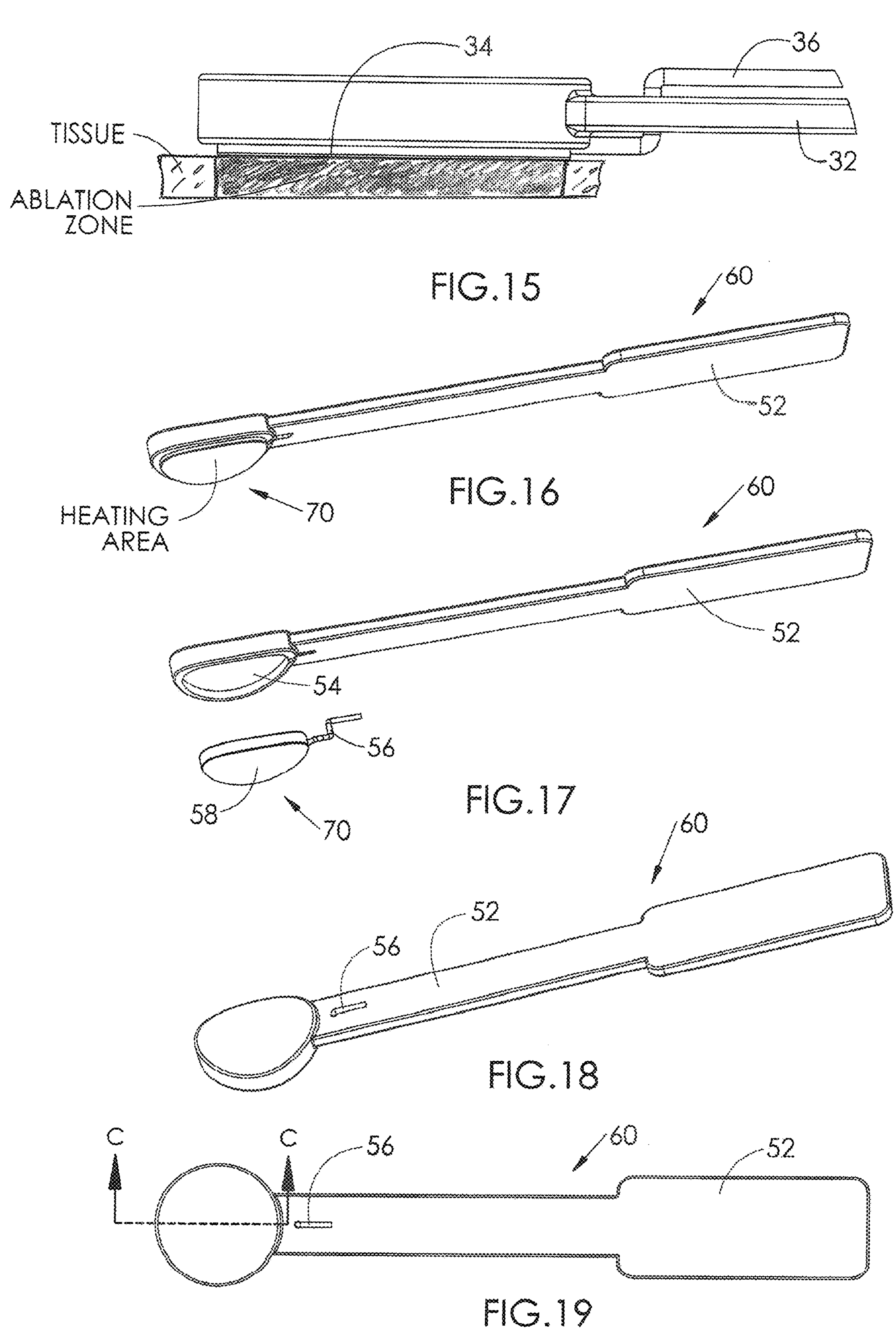
FIG. 15 is a view of the planar applicator device assembly (40), shown with the heating elements (50) contacting a target tissue region and depicting an illustrative example of the resulting tissue ablation zone.
FIG. 16 illustrates a perspective view of one embodiment of the planar applicator device assembly (60), wherein the heating element elements (70) is formed with a dome-shaped, convoluted profile to enhance uniform energy distribution across the contacted tissue region.
FIG. 17 is an exploded view of planar applicator device assembly (60).
FIG. 18 illustrates another perspective view of the planar applicator device assembly (60).
FIG. 19 is a top view of planar applicator device assembly (60).

FIG. 15 illustrates a view of the planar applicator device assembly (40) engaging and compressing a target tissue region, and depicts an illustrative example of a resulting tissue ablation zone. The ablation zone corresponds to the region of thermal energy delivered by the heating element (34), which is generated by microwave energy distributed within the heating body by the internal microwave antenna. The illustrated ablation zone demonstrates controlled, uniform, and reproducible thermal treatment across the tissue area contacted by the heating element.

FIGS. 16, 17, 18, and 19 illustrate an alternative embodiment of a planar applicator device assembly (60) configured in a manner analogous to the previously described planar applicator device assembly (40). In this embodiment, the planar applicator assembly (60) includes a heating element (70) secured to a mating feature (54) of an applicator body (52).

Figures 20, 21, 22, 23, 24, 25, 26:
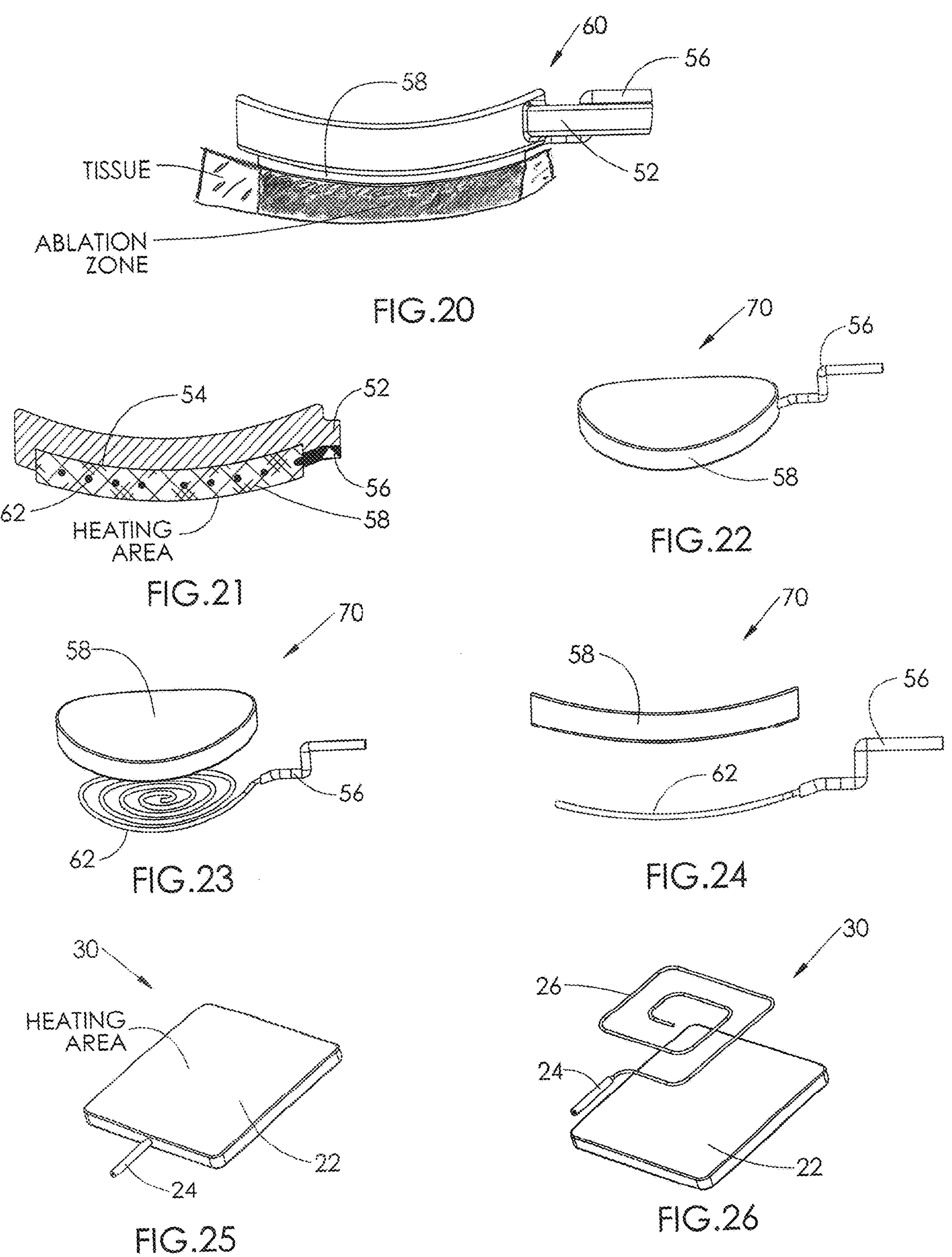
FIG. 20 is a view of the planar applicator device assembly (60), shown with the heating elements (70) contacting a target tissue region and depicting an illustrative example of the resulting tissue ablation zone.
FIG. 21 is a cross-sectional view taken along line C-C from FIG. 21.
FIG. 22 illustrates a perspective view of heating elements (70).
FIG. 23 is a perspective exploded view of heating elements (70).
FIG. 24 is a front exploded view of heating assembly (70).
FIG. 25 illustrates a perspective view of rectangular heating elements (30), according to one embodiment of the present invention.
FIG. 26 is an exploded view of rectangular heating elements (30).

The heating element (70) includes a heating body (58) having a curved or dome-shaped profile configured to better conform to and engage curved target tissue regions. As illustrated in FIG. 20, the dome-shaped profile of the heating body (58) is adapted to conform to a curved tissue surface, thereby promoting uniform contact, efficient thermal coupling, and consistent delivery of thermal energy across the entire curved tissue area to be heated and ablated.

FIGS. 21, 22, 23, and 24 illustrate a configuration of the heating element (70) in which a curved, dome-shaped heating body (58) is shown with a spiral microwave antenna (62) disposed within the heating body (58). The profile of the microwave antenna (62) is configured to follow the curved, dome-shaped profile of the heating body (58) in order to distribute microwave energy substantially uniformly throughout the entire volume of the microwave-absorbing material of the heating body (58).

It will be understood that, for different curved or dome-shaped profiles of the heating body (58), the microwave antenna (62) may be correspondingly structured, shaped, or arranged to ensure delivery of microwave energy to substantially the entire volume of the microwave-absorbing material, thereby providing consistent and uniform heating of the target tissue area.

Such curved or dome-shaped heating element configurations are particularly advantageous for ablating non-planar anatomical tissue surfaces, including but not limited to lung, liver, bowel, and other organs having curved or irregular geometries, where uniform surface contact and consistent thermal delivery across the tissue interface are desirable.

FIGS. 25 and 26 illustrate a configuration of a heating element assembly (30) in which a heating body (22) has a generally rectangular shape. A microwave antenna (26), such as a spiral microwave antenna, is disposed within the heating body (22). The profile of the microwave antenna (26) is configured to follow the rectangular profile of the heating body (22) in order to distribute microwave energy substantially uniformly throughout the entire volume of the microwave-absorbing material of the heating body (22).

It will be understood that, for different rectangular or non-cylindrical profiles of the heating body (22), the microwave antenna (26) may be correspondingly structured, shaped, or arranged to ensure delivery of microwave energy to substantially the entire volume of the microwave-absorbing material, thereby providing consistent and uniform heating of the target tissue area.

Such rectangular heating element configurations may be incorporated into forceps-based devices or planar applicator devices as described herein to enable controlled, uniform, and reproducible ablation across a defined tissue contact area.

Figure 27:
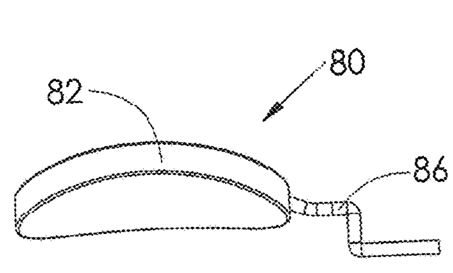
FIG. 27 illustrates a perspective view of one embodiment of the spatula-shaped heating elements (80).
Figure 28:
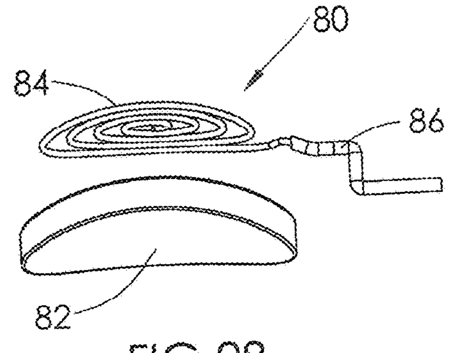
FIG. 28 is a front exploded view of heating elements (80).
Figure 29:
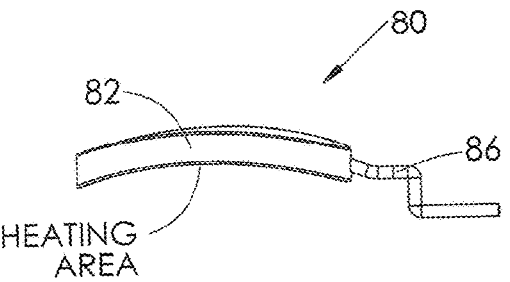
FIG. 29 is a front view of heating elements (80).

FIGS. 27, 28, and 29 illustrate a heating element assembly (80) in which a heating body (82) includes a bent or curved internal profile. A microwave antenna (84) is disposed within the heating body (82) and is configured to follow the internal curved profile of the heating body (82) to distribute microwave energy substantially uniformly throughout the volume of the microwave-absorbing material. A coaxial cable (86) supplies microwave energy from a microwave energy source to the microwave antenna (84).

Figure 30:
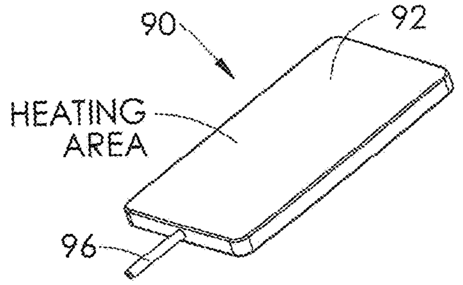
FIG. 30 illustrates a perspective view of one embodiment of the rectangular heating elements (90) incorporating a zig-zag-shaped microwave antenna.
Figure 31:
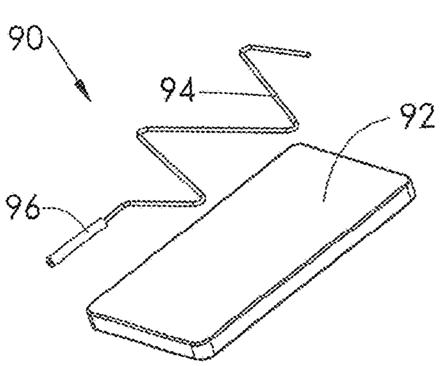
FIG. 31 is an exploded view of heating elements (90).

FIGS. 30 and 31 illustrate a heating element assembly (90) in which a heating body (92) has a generally rectangular shape and incorporates a zig-zag or serpentine microwave antenna (94) disposed within the heating body (92). The microwave antenna (94) is configured to distribute microwave energy substantially uniformly throughout the microwave-absorbing material. A coaxial cable (96) supplies microwave energy to the microwave antenna (94).

Figure 32:
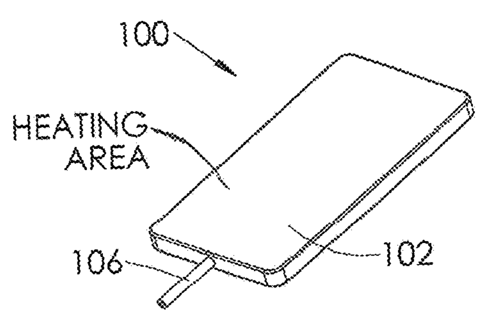
FIG. 32 illustrates a perspective view of one embodiment of the rectangular heating elements (100) incorporating a flat microwave antenna.
Figure 33:
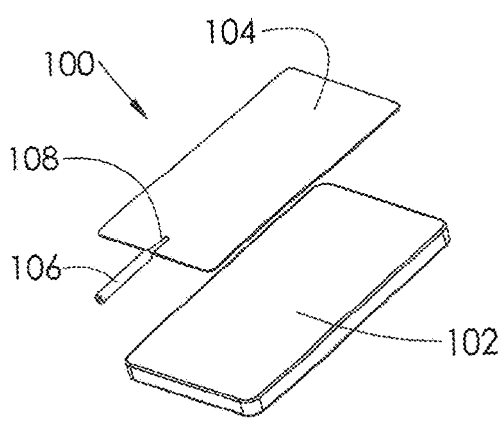
FIG. 33 is an exploded view of heating elements (100).

FIGS. 32 and 33 illustrate a heating element assembly (100) in which a heating body (102) incorporates a linear microwave antenna or a microstrip patch antenna (104) disposed within the heating body (102). A cable (106) supplies microwave energy to the microwave antenna (104) via an electrical connection (108), such as a soldered, welded, or otherwise electrically bonded connection.

It will be understood that, using known engineering principles, a wide variety of microwave antenna configurations may be incorporated within the heating elements described herein, including but not limited to spiral, serpentine, zig-zag, loop, linear, planar, curved, or microstrip antenna structures. Such antenna configurations may be selected and adapted to follow the geometry of the heating body in order to deliver microwave energy to substantially the entire volume of the microwave-absorbing material, thereby providing controlled, uniform, and reproducible thermal effects across a defined tissue area.

In further embodiments, the heating elements described herein may incorporate additional microwave antenna configurations selected to distribute microwave energy uniformly throughout the microwave-absorbing material of the heating body. Such additional antenna configurations include, but are not limited to:

(i) a loop or folded-loop microwave antenna, configured to encircle or partially encircle a portion of the heating body volume;

(ii) a meander-line microwave antenna, having a repeating folded or undulating conductive path adapted to increase energy distribution density within the heating body; and.

(iii) a planar slot or aperture-coupled microwave antenna, formed as a conductive or patterned structure adapted to couple microwave energy into the microwave-absorbing material.

Each of these antenna configurations may be structured to follow the external or internal geometry of the corresponding heating body, including planar, rectangular, curved, dome-shaped, or compound profiles, to ensure delivery of microwave energy to substantially the entire volume of the microwave-absorbing material.

Any of the microwave antenna configurations described herein—including spiral, serpentine, zig-zag, linear, microstrip patch, loop, folded-loop, meander-line, or slot-type antennas—may be incorporated into heating elements used with forceps-based devices or planar applicator devices, thereby enabling controlled, uniform, and reproducible ablation across planar or non-planar tissue areas.

Further embodiments, modifications, and substitutions that would be apparent to one of ordinary skill in the art are within the scope of the present invention, which is limited only by the claims that follow.

What is claimed is:

1. An apparatus for use as a working end of a surgical instrument, comprising:

a first jaw member and a second jaw member movable relative to one another between an open position and a closed position;

a heating element disposed within at least one of the first or second jaw members, the heating element comprising a microwave-absorbing material and defining a heating area dimensioned to cover a targeted tissue area;

a microwave antenna disposed entirely within the microwave-absorbing material of the heating element, wherein the microwave antenna has a non-linear, area-distributed geometry configured to extend across at least two dimensions of the heating area so as to distribute microwave energy substantially uniformly throughout the microwave-absorbing material; and a coaxial cable configured to couple the microwave antenna to a source of microwave energy;

wherein the microwave antenna, by virtue of its non-linear, area-distributed geometry extending across at least two dimensions of the heating area, is configured to distribute microwave energy substantially uniformly throughout the heating area of the heating element to provide uniform thermal energy delivery to the targeted tissue area.

2. The apparatus of claim 1, wherein the heating element has a geometry selected from a planar shape, a rectangular shape, a curved shape, a dome-shaped profile, an oval shape, or a compound surface shape configured to conform to a planar or non-planar tissue surface.

3. The apparatus of claim 2, wherein the microwave antenna has a two-dimensional or three-dimensional geometry configured to follow the shape of the heating element across its full extent, such that microwave energy is distributed substantially uniformly throughout the microwave-absorbing material, in contrast to a linear antenna element extending only along a single axis of the heating element.

4. The apparatus of claim 1, wherein the microwave antenna comprises at least one of a spiral antenna, serpentine antenna, zig-zag antenna, loop antenna, folded-loop antenna, or meander-line antenna, each having a geometry that traverses at least two dimensions of the heating area to provide area-distributed energy delivery throughout the microwave-absorbing material.

5. The apparatus of claim 1, wherein the first and second jaw members are configured to compress the targeted tissue area while the heating element delivers uniform thermal energy across the targeted tissue area.

6. The apparatus of claim 1, wherein the heating element is incorporated into a planar applicator device configured to contact a planar or non-planar tissue surface for area tissue ablation.

7. The apparatus of claim 1, wherein the microwave-absorbing material comprises a polymeric or elastomeric matrix impregnated with one or more microwave-absorbing fillers selected from conductive, magnetic, or dielectric particles.

8. The apparatus of claim 1, wherein the heating element includes a surface coating configured to reduce tissue adhesion and facilitate cleaning or sterilization.

9. The apparatus of claim 1, wherein the heating element is secured to the jaw member by at least one of an adhesive bond, an epoxy, a press-fit engagement, an interference fit, a mechanical fastener, an overmolding process, or a combination thereof.

10. An apparatus for ablating a targeted tissue area, comprising:

an applicator body having a distal portion configured to contact a tissue surface;

a heating element disposed at the distal portion of the applicator body, the heating element comprising a microwave-absorbing material and defining a heating area dimensioned to cover a targeted tissue area;

a microwave antenna disposed entirely within the microwave-absorbing material of the heating element, wherein the microwave antenna has a non-linear, area-distributed geometry configured to extend across at least two dimensions of the heating area so as to distribute microwave energy substantially uniformly throughout the microwave-absorbing material; and a cable configured to couple the microwave antenna to a source of microwave energy;

wherein the microwave antenna, by virtue of its non-linear, area-distributed geometry extending across at least two dimensions of the heating area, is configured to distribute microwave energy substantially uniformly throughout the heating area of the heating element to provide uniform thermal energy delivery to the targeted tissue area.

11. The apparatus of claim 10, wherein the heating element has a geometry selected from a planar shape, a rectangular shape, a curved shape, a dome-shaped profile, an oval shape, or a compound surface shape configured to conform to a planar or non-planar tissue surface.

12. The apparatus of claim 11, wherein the microwave antenna has a geometry configured to follow the geometry of the heating element such that microwave energy is distributed substantially uniformly throughout the microwave-absorbing material.

13. The apparatus of claim 10, wherein the microwave antenna comprises at least one of a spiral antenna, serpentine antenna, zig-zag antenna, loop antenna, folded-loop antenna, meander-line antenna, linear antenna, microstrip patch antenna, or slot-type antenna.

14. The apparatus of claim 10, wherein the heating element is configured to conform to a non-planar anatomical tissue surface to provide uniform thermal energy delivery across a curved or irregular tissue area.

15. The apparatus of claim 10, wherein the distal portion of the applicator body is configured to contact and optionally compress the targeted tissue area during delivery of thermal energy.

16. The apparatus of claim 10, wherein the heating element is configured to ablate non-planar anatomical tissue regions including lung, liver, bowel, or other curved or irregular tissue surfaces.

17. A method of ablating a targeted tissue area, comprising:

positioning a heating element comprising a microwave-absorbing material in contact with a targeted tissue area, the heating element defining a heating area dimensioned to cover the targeted tissue area;

delivering microwave energy from a microwave energy source through a cable to a microwave antenna disposed entirely within the microwave-absorbing material, wherein the microwave antenna has a non-linear, area-distributed geometry extending across at least two dimensions of the heating area;

distributing the microwave energy substantially uniformly throughout the microwave-absorbing material by the area-distributed geometry of the microwave antenna; and converting the distributed microwave energy into thermal energy within the heating element to uniformly heat and ablate the targeted tissue area.

18. The apparatus of claim 17, further comprising compressing the targeted tissue area prior to or during delivery of microwave energy to improve thermal coupling and ablation uniformity.

19. The apparatus of claim 17, wherein distributing microwave energy comprises shaping the microwave antenna to follow geometry of the heating element.

20. The apparatus of claim 17, wherein the heating element contacts a planar tissue surface or a non-planar tissue surface during ablation.

* * * * *